United States Patent [19]

Herrle et al.

[11] Patent Number: 5,288,409
[45] Date of Patent: Feb. 22, 1994

[54] INHIBITING THE GROWTH OF ZEBRA MUSSELS

[75] Inventors: Richard P. Herrle, Greentree Boro; Virginia Piermattie, Pittsburgh, both of Pa.

[73] Assignee: Aristech Chemical Corporation, Pittsburgh, Pa.

[21] Appl. No.: 42,501

[22] Filed: Apr. 2, 1993

[51] Int. Cl.$^5$ .......... C02F 1/50; A01N 25/00; A01N 25/10

[52] U.S. Cl. .......... 210/698; 210/764; 106/16; 106/18.32; 405/211; 424/78.09; 424/405; 424/409; 422/6

[58] Field of Search .......... 106/16, 18.32; 424/78.09, 405, 409; 210/696, 764, 698; 405/211; 422/6

[56] References Cited

U.S. PATENT DOCUMENTS

| | | | |
|---|---|---|---|
| 4,111,879 | 9/1978 | Mori et al. | 260/29.6 N |
| 4,579,665 | 4/1986 | Davis et al. | 210/755 |
| 4,653,584 | 3/1987 | Ball et al. | 252/8.551 |
| 4,816,163 | 3/1989 | Lyons et al. | 210/698 |
| 4,826,685 | 5/1989 | Stewart | 424/409 |
| 4,857,209 | 8/1989 | Lyons et al. | 210/755 |
| 4,906,385 | 3/1990 | Lyons et al. | 210/698 |
| 4,970,239 | 11/1990 | Whitekettle et al. | 514/665 |
| 4,983,669 | 1/1991 | Piermattie et al. | 525/47 |
| 5,015,395 | 5/1991 | Muia et al. | 210/755 |
| 5,040,487 | 8/1991 | Bollyky et al. | 119/4 |
| 5,062,967 | 11/1991 | Muia et al. | 210/755 |
| 5,096,601 | 3/1992 | Muia et al. | 210/755 |
| 5,128,050 | 7/1992 | Gill | 210/755 |
| 5,141,754 | 8/1992 | Ekis, Jr. et al. | 424/661 |

OTHER PUBLICATIONS

Eugene C. Fischer et al, "Technology for Control of Marine Biofouling-A Review", Marine Biodeterioration-An Interdisciplinary Study, pp. 261-299, 1984.

*Primary Examiner*—Neil M. McCarthy
*Attorney, Agent, or Firm*—William L. Krayer

[57] ABSTRACT

Growth of zebra mussels on a surface is inhibited by making the surface from an unsaturated polyester having copolymerized therein about 1-40% N-phenyl maleimide.

2 Claims, No Drawings

INHIBITING THE GROWTH OF ZEBRA MUSSELS

TECHNICAL FIELD

This invention relates to the inhibition of the growth of zebra mussels (Dreissena Polymorpha) which have recently infested the Great Lakes and nearby rivers and other waters. It involves the use of certain thermosetting materials as structural or surface materials in areas where the zebra mussels are not desired. The areas of concern can be either stationary, such as piers, power plant cooling water intakes, and the like, or moving, such as boat hulls or buoys. The thermosetting materials are unsaturated polyesters copolymerized with N-phenyl maleimide or N-cyclohexyl maleimide.

BACKGROUND OF THE INVENTION

Zebra mussels were first discovered in American waters in Lake St. Clair in 1988, ["Infestation of the Monroe Power Plant by the Zebra Mussel (Dreissena Polymorpha)", Kovalack, W. P., Longton, G. D., Smithee, R. D., Proceedings of the American Power Conference, Chicago, Ill., 1990]. It is believed that the mussel larvae were dumped into the water with a European or Western Asian ship's ballast water in 1985. The mussels have spread quickly throughout the Great Lakes Basin and are reasonably expected to infest waterways in most of the United States including Florida but excluding most of the other Southern and Southwestern states and to infest most of southern Canada. They have spread throughout most of Europe with the exception of northern Scandinavia, the Iberian Peninsula and Italy. They are also in western Asia where they originally inhabited the Ural River and Caspian Sea but now cover almost all of Russia, extending into Turkey ["Impact of the European Zebra Mussel Infestation to the Electric Power Inudstry", McMahon, R. F., Tsou, J. L., Proceedings of the American Power Conference, Chicago, Ill., 1990].

Zebra mussels float through the waters in a free swimming planktonic veliger state. They attach to any hard surface with byssal threads. The byssus contains up to 200 threads which are difficult to remove from a surface even after death. They may attach to other mussel shells and form large clumps of mussels which threaten to block intake lines of raw water supplying power plants and municipal water authorities ["Control of Zebra Mussels at CEI Facilities", Barton, L. K., Proceedings of the American Power Conference, Chicago, Ill., 1990].

Workers in the art have attempted to control macroinvertebrates generally by dissolving into the environment of the target organisms various amines and/or quaternaries. See, for example, U.S. Pat. No. 4,816,163 to Lyons et al, U.S Pat. No. 4,857,209 to Lyons et al, U.S. Pat. No. 4,906,385 to Lyons et al, U.S. Pat. No. 4,970,239 to Whitekettle et al, and U.S. Pat. No. 4,579,665 to Davis et al. When zebra mussels received attention, they also were attacked through the use of various water-soluble materials, such as the halides of Ekis, Jr. et al U.S. Pat. No. 5,141,754, the particular quaternary ammonium compounds of Gill in U.S. Pat. No. 5,128,050, and Muia et al in U.S. Pat. No. 5,062,967, and the quaternary ammonium polymers of Muia et al in U.S. Pat. Nos. 5,015,39 and 5,096,601. Bollyky et al in U.S. Pat. No. 5,040,487 use ozone. All such approaches are to treat the aqueous environment in which the zebra mussels live.

Generally, the environments treated are open to circulation of water, and accordingly, the maintenance of an effective concentration of such materials requires continuous or frequent feeding, which means a risk must be calculated as to the tolerance of other living things in the environment for the materials introduced, even if the effective concentrations to be maintained are relatively low.

SUMMARY OF THE INVENTION

We have found that zebra mussels are reluctant to settle on surfaces made of a complex polymer or resin comprising about 5% to about 89% of a more or less conventional unsaturated polyester, about 1–40% by weight of a maleimide, up to about 20% of methacrylic acid or a lower ester thereof, and about 10–40% of a polymerizable monomer such as styrene or vinyl toluene. Various generally inert fillers such as kaolin clay, aluminum trihydrate, calcium carbonate, glass fibers and the like may be added to the resin depending on the physical properties desired. Where the maleimide is N-phenyl maleimide, the compositions may be as described in Piermattie et al U.S. Pat. No. 4,983,669; this patent also contains a description of the unsaturated polyesters useful in our invention, and accordingly, the entire specification of U.S. Pat. No. 4,983,669 is incorporated herein by reference.

DETAILED DESCRIPTION OF THE INVENTION

Example 1

In a controlled laboratory experiment, approximately 113 mussels in the form of adults were placed in boxes which were set in a temperature controlled aquarium. They were given the choice of attaching to a vertical wall of the box constructed of polystyrene, a panel of cured polyester containing either 3% or 10% by weight copolymerized N-phenylmaleimide, other mussel shells or not attaching at all. After three weeks, the results were:

|  | 3% NPM | 10% NPM | Polystyrene | Shells | Floating |
|---|---|---|---|---|---|
| # Mussels attached | 4 | 0 | 54 | 20 | 35 |

Example 2

In a controlled laboratory experiment, 51 mussels were placed in each of several boxes which were set in a temperature controlled aquarium. Boxes were made up of either polystyrene, polystyrene lined with panels made up of 3% NPM-polyester panels or polystyrene lined with 10% NPM-polyester panels, so that the mussels did not have a choice of surface on which to settle.

Mussels attach to vertical surfaces first by extending long, thick byssal threads which seem to be temporary. Later they extend short, thinner permanent threads to the surface. The results (average number of threads per mussel) of this experiment which lasted for six weeks are:

|  | 3% NPM Box | 10% NPM Box | Polystyrene Box |
| --- | --- | --- | --- |
| total threads | 85.9 | 80 | 36.7 |
| type of thread |  |  |  |
| temp. | 35.1 | 29.4 | 5.6 |
| perm. | 50.8 | 50.6 | 31.1 |

Example 3

Through the use of a Scanning Electron Microscope, the point of attachment of the byssal thread to the surface could be observed, filmed and photographed. The threads open up to a uniform circular foot referred to as a plaque which is the point of attachment. The plaques on the polystyrene surfaces were in fact circular and uniform. All of the plaques on the panels which incorporated NPM into the polyester had jagged irregular perimeters and were non-uniform. We conclude that for an as yet unknown reason, the material that we have developed affects the nature of attachment.

We claim:

1. A method of inhibiting the settling of zebra mussels on a surface in an aqueous environment comprising contacting said aqueous environment with said surface which comprises a cured, copolymerized, resin composition comprising about 5-89% unsaturated polyester, about 1-40% N-phenyl maleimide, up to about 20% methacrylic acid or a lower alkyl ester thereof, and about 10-40% of a polymerizable monomer.

2. Method of claim 1 wherein the polymerizable monomer is styrene.

* * * * *